(12) United States Patent
Casoni

(10) Patent No.: US 12,016,831 B2
(45) Date of Patent: Jun. 25, 2024

(54) POLIDOCANOL FOR USE AS IMMUNOMODULATING AGENT

(71) Applicant: Paolo Casoni, Parma (IT)

(72) Inventor: Paolo Casoni, Parma (IT)

( * ) Notice: Subject to any disclaimer, the term of this patent is extended or adjusted under 35 U.S.C. 154(b) by 395 days.

(21) Appl. No.: 15/734,825

(22) PCT Filed: Jun. 5, 2019

(86) PCT No.: PCT/EP2019/064703
§ 371 (c)(1),
(2) Date: Dec. 3, 2020

(87) PCT Pub. No.: WO2019/234120
PCT Pub. Date: Dec. 12, 2019

(65) Prior Publication Data
US 2021/0228503 A1 Jul. 29, 2021

(30) Foreign Application Priority Data
Jun. 7, 2018 (IT) .................. 102018000006109

(51) Int. Cl.
| | | |
|---|---|---|
| *A61K 31/08* | (2006.01) | |
| *A61P 17/00* | (2006.01) | |
| *A61P 23/02* | (2006.01) | |
| *A61P 29/00* | (2006.01) | |
| *A61P 29/02* | (2006.01) | |
| *A61P 37/02* | (2006.01) | |

(52) U.S. Cl.
CPC .............. *A61K 31/08* (2013.01); *A61P 17/00* (2018.01); *A61P 23/02* (2018.01); *A61P 29/00* (2018.01); *A61P 29/02* (2018.01); *A61P 37/02* (2018.01)

(58) Field of Classification Search
CPC .................................. A61K 31/08; A61P 23/02
See application file for complete search history.

(56) References Cited

U.S. PATENT DOCUMENTS

| | | | |
|---|---|---|---|
| 6,217,885 B1 | 4/2001 | Röder et al. | |
| 8,440,234 B2 * | 5/2013 | Kim ..................... | A61P 19/02 424/539 |
| 2003/0027833 A1* | 2/2003 | Cleary ................. | A61K 9/7015 514/270 |
| 2009/0202467 A1 | 8/2009 | Bock | |

FOREIGN PATENT DOCUMENTS

| | | | |
|---|---|---|---|
| EP | 0 656 203 A1 | 6/1995 | |
| WO | WO 00/72821 A1 | 12/2000 | |
| WO | WO 02/053145 A1 | 7/2002 | |
| WO | WO-02053145 A1 * | 7/2002 | ............. A61K 31/77 |
| WO | WO 2004/062461 A2 | 7/2004 | |
| WO | WO 2016/138136 A1 | 9/2016 | |
| WO | WO 2017/028976 A1 | 2/2017 | |
| WO | WO-2017028976 A1 * | 2/2017 | ........... A61K 31/167 |
| WO | WO 2017/207520 A1 | 12/2017 | |
| WO | WO 2018/020436 A1 | 2/2018 | |

OTHER PUBLICATIONS

Smith et al., The importance of bicarbonate in large volume anesthetic preparations. Revisiting the tumescent formula, J Dermatol Surg Oncol. Nov. 1992;18(11):973-5.*
Szczepanski, Long-term effectiveness of polidocanol synoviorthesis of knee joint in the treatment of the refractory rheumatoid effusions, Jan. 2001, Reumatologia/ Rheumatology 39(3):246-252.*
Sarzi-Puttini, Pain in rheumatoid arthritis: a critical review, Reumatismo, Jun. 6, 2014;66(1):18-27.*
Polidocanol (Asclera® and Varithena®), National Drug Monograph, May 2014, available at file:///C:/Users/sivanova/Downloads/FDA-2018-N-3240-0277_attachment_20.pdf.*
Dorothea Schweiger, et al., "Efficacy of a New Tonic Containing Urea, Lactate, Polidocanol, and *Glycyrrhiza inflate* Root Extract in the Treatment of a Dry, Itchy, and Subclinically Inflamed Scalp", Skin Pharmacology and Physiology, XP 9511666A, (2013), 12 pages.
Staffan Jahnson, et al., "Modulation of the inflammatory response after sclerotherapy for hydrocoele/spermatocoele", BJU International (BJUI), XP 9511665A, (2018), 8 pages.
Bo Eklöf, et al., "Revision of the CEAP classification for chronic venous disorders: Consensus statement", Journal of Vascular Surgery, vol. 40, No. 6, (2004), pp. 1248-1252.
R. Launois, et al., "Construction and validation of a quality of life questionnaire in Chronic Lower Limb Venous Insufficiency (CIVIQ)", Quality of Life Research, vol. 5, (1996), pp. 539-554.
Nizar Elleuch, et al., "Sulodexide in Patients with Chronic Venous Disease of the Lower Limbs: Clinicai Efficacy and Impact on Quality of Life", Adv. Ther., (2016), 14 pages.
European Office Action dated Apr. 5, 2023 in European Patent Application No. 19 732 915.4-1112, 7 pages.
Combined Chinese Office Action with Search Report dated Apr. 5, 2023 in Chinese Patent Application No. 201980038089.1 (with English translation), 18 pages.
Anonymous: "Asclera (polidocanol) Injection, for intravenous use" Mar. 1, 2010 (Mar. 1, 2010), pp. 1-8, XP055508022, Retrieved from the Internet: URL:https://www.accessdata.fda.gov/drugsatfda_docs/label/ 2010/021201 lbl.pdf [retrieved on Sep. 19, 2018].
Duffy D M et al: "The role of sclerotherapy in abnormal varicose hand veins", Plastic and Reconstructive Surgery Oct. 1999 US, vol. 104, No. 5, Oct. 1999 (Oct. 1999), pp. 1474-1479,ISSN: 0032-1052.
Eckmann David M: "Polidocanol for endovenous microfoam sclerosant therapy",Expert Opinion on Investigational Drugs, vol. 18, No. 12, Nov. 25, 2009 (Nov. 25, 2009), pp. 1919-1927, XP093036205,UK ISSN: 1354-3784, DOI: 10.1517/13543780903376163.

(Continued)

*Primary Examiner* — Svetlana M Ivanova
(74) *Attorney, Agent, or Firm* — Oblon, McClelland, Maier & Neustadt, L.L.P.

(57) ABSTRACT

The present invention relates to the use of diluted, thus non-sclerosing, polidocanol solutions as immunomodulating and anti-inflammatory agents. The inventions further relates to non-sclerosing compositions 5 comprising polidocanol in concentration of from 0.03 to 0.10% w/V for the treatment of psoriatic skin rashes, for cosmetic use and for the reduction of peripheral venous stasis.

9 Claims, 5 Drawing Sheets

(56) References Cited

OTHER PUBLICATIONS

Yu Chuanlong, et al., eds., "Common Knowledge Evidence", China Health Media Group, China MedTech Publishing House, Aug. 31, 2018, pp. 1994-1995 (7 total pages) (with English translation).
Office Action issued on Mar. 14, 2024, in Australia Patent Application No. 2019282279.

* cited by examiner

A          B

POLIDOCANOL FOR USE AS IMMUNOMODULATING AGENT

FIELD OF THE INVENTION

The present invention relates to the use of diluted polidocanol for systemic administration and to its use as an immune and inflammatory response modulator.

PRIOR ART

Polidocanol, or PEG-9 lauryl alcohol, is a lauryl alcohol polyethylene glycol ether with a mean value of ethylene oxide units equal to 9. It belongs to the class of non-ionic surfactants and it is represented by the structural formula depicted below:

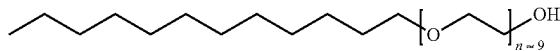

The compound has been widely used in the past as additive/excipient in different formulations and for a wide array of applications.

The use of polidocanol as local anaesthetic and antipruritic agent begun around 1950, and it is still used at present in topical formulations, for example in the treatment of dermatitis, eczema and insect bites.

Polidocanol was used for the first time in the 60's as a sclerosant for the treatment of small varicose veins and reticular varices. At present it is mainly used for this purpose and it can be found as a hydroalcoholic solution (0.25-3% polidocanol, e. g. Asclera and Atossisclerol), or as an aqueous micro-foam (0.5-1% polidocanol, e. g. Varithena).

Polidocanol, as well-known, has been used for many years as sclerosant for varicose veins reduction. The sclerosing effect is carried out through cellular damage activated by the increase of the cellular calcium and of the nitric oxide pathway, which results in the death of the treated vessel's endothelial cells. At times, the damage can involve the red blood cells, leading to haemolysis, or the platelets with the formation of small blood clots.

Applications and patents describing polidocanol, mainly as a sclerosant, but also as lipolytic or antipruritic agent for local application, have been identified in the patent literature. U.S. Pat. No. 6,217,885B1 (Bayer Aktiengesellschaft) discloses polidocanol based compositions for topical application as antipruritic agents. The disclosed compositions comprise polidocanol, an astringent agent and one or more anti-inflammatory substances.

Generally, foams are the preferred polidocanol formulations for the sclerosant treatment, having the advantage of avoiding the immediate dilution of the agent in the vessel bloodstream. For example, patent EP0656203B1 (BTG International Limited) discloses a sclerosant based micro-foam for the treatment of varicose veins. The micro-foam is obtained mixing an aqueous solution of the sclerosant and a gas. Polidocanol is one of the particularly preferred sclerosants. In particular, the patent claims a micro-foam comprising a sclerosant and oxygen, or a mixture of oxygen and carbon dioxide, as a gas.

The application WO2000/72821 (BTG International Limited) discloses sclerosant comprising micro-foam compositions, methods of production thereof and administration devices thereof. The compositions are preferably polidocanol based aqueous solutions at a concentration of 0.5-4 vol. %.

Also WO2004/062461 discloses sclerosing micro-foams based on polidocanol aqueous solutions, with a 0.25-5% concentration.

International patent application WO2016/138136A1, on the other hand, discloses pharmaceutical compositions comprising polidocanol and a C3-C6 alcohol used for the elimination of adipose tissue via subcutaneous injection.

To the best of the Applicant's knowledge, useful effects of polidocanol concentrations below 0.25% have never been demonstrated, nor has it ever been disclosed the use of polidocanol in improving skin trophism, the hair appearance, or its immunomodulating effect. Even the lipolytic activity on fat tissue, disclosed in WO2016/138136A1, is obtained at polidocanol concentrations of between 0.5 and 2%. Also WO2017/207520, of Chemische Fabrik Kreussler, mentions the use of hydroalcoholic solutions of polidocanol in a concentration of between 0.1 and 20% for the treatment of localized fatty tissue.

WO2017/028976 discloses the use of compositions comprising polidocanol as local anaesthetic for the treatment of inflammation of the oral cavity in combination with *Althaea officinalis* L in concentration of from 0.001 to 5% w/V.

SUMMARY OF THE INVENTION

The present invention relates to a polidocanol solution with a concentration of from 0.03 to 0.10% by weight, for use as immunomodulating and anti-inflammatory agent. Preferably, the polidocanol concentration is of from 0.04 to 0.08%, more preferably of from 0.05%-0-06% in a physiological saline solution (0.9% w/V NaCl). According to a preferred embodiment, the solution of polidocanol diluted in physiological saline comprises a buffer, more preferably a bicarbonate buffer, in concentration below 0.07% w/V, even more preferably of from 0.05 to 0.06%.

According to another aspect, the invention relates to the immunomodulating and anti-inflammatory effect of polidocanol solutions at the abovementioned concentrations and is measured in vitro on a blood sample formerly taken and comprises the measurement of one or more cytokines, chemokines and/or growth factors selected from the group consisting of: VEGF, IgG, IgA, IgM, IL-1 ra, IL-1β, IL-7 and IL-8. According to a further aspect, the invention relates to polidocanol compositions in non-sclerosing concentration, of from 0.03 to 0.10%, or more preferably of from 0.04 to 0.09% by weight, for use as immune system activator and anti-inflammatory agent. Polidocanol compositions in non-sclerosing concentration, of from 0.05 to 0.06%, are particularly preferred. Moreover, compositions comprising polidocanol in concentration of from 0.03 to 0.10% by weight, or more preferably of from 0.04 to 0.09% by weight, can also be used cosmetically, in particular to improve the skin trophism and ameliorate or reduce the venous stasis.

DETAILED DESCRIPTION OF THE INVENTION

Figure 1:
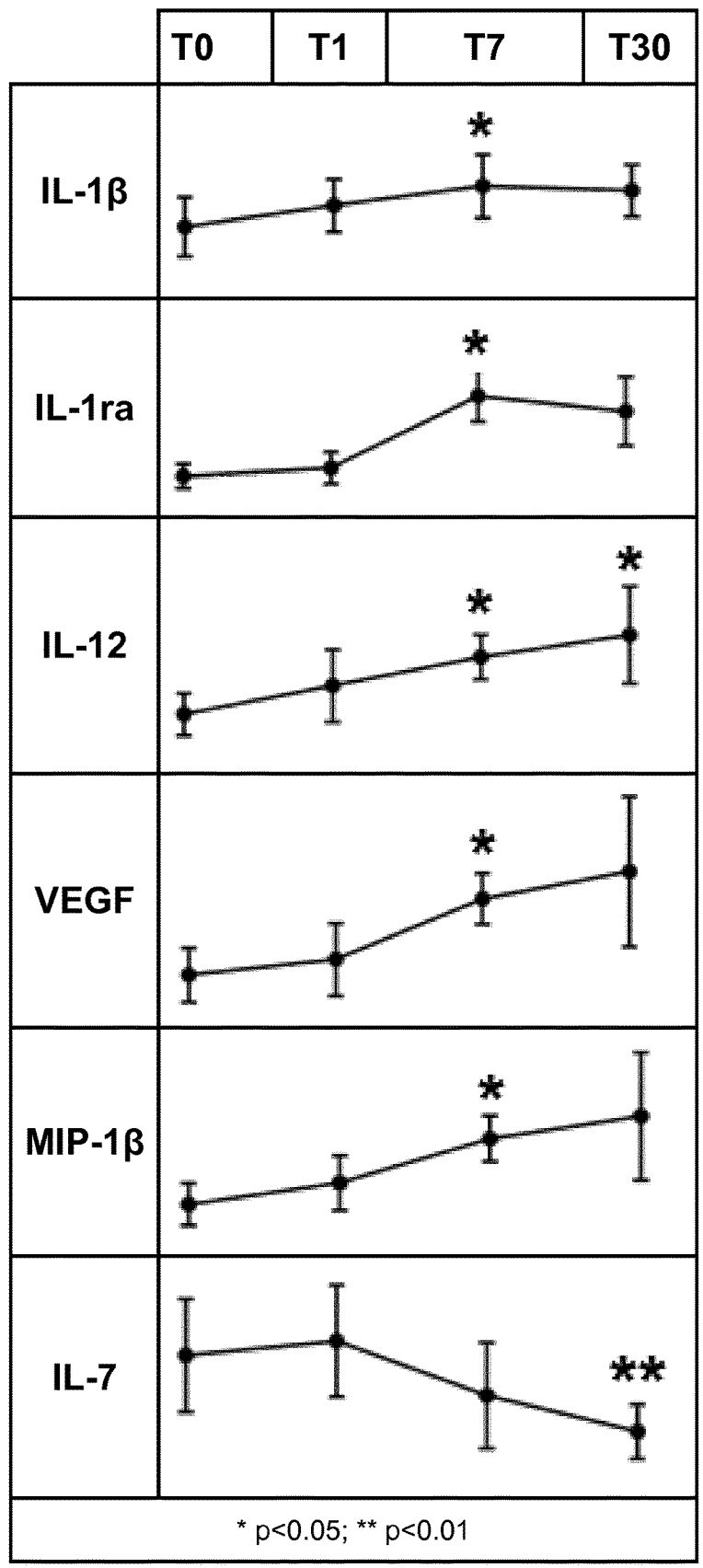
FIG. 1. Measurement of cytokines and growth factors levels at time zero (T0), one day (T1), 7 days (T7) and 30 days (T30) after treatment with diluted polidocanol according to the invention.

The present invention relates to the systemic use of a polidocanol solution in concentration below 0.10% by weight (low-concentration polidocanol), preferably of from 0.03 to 0.09%, preferably of from 0.04 to 0.08%, more preferably 0.05-0.06% in saline solution (0.9% w/V NaCl) for use as immunomodulating and anti-inflammatory agent.

The diluted polidocanol solution according to the invention does not exert a sclerosing effect: therefore it does not result in venous, reticular or capillary parietal damage. It is administered parenterally via the intravenous route. On the other hand, notably, polidocanol concentrations higher or equal to 0.12% do have a sclerosing effect on small calibre capillaries or reticular veins and parietal damage.

The polidocanol solution, in the dosage according to the present invention, has immunomodulating and anti-inflammatory activity.

According to further embodiments diluted polidocanol improves the condition of patients suffering from peripheral venous stasis; furthermore, it has been found to improve the osteoarticular pain and the articular mobility of people aged over 70. Moreover, its use, for at least 4 applications every two months, contributes in determining a higher overall well-being, associated with an anti-inflammatory activity and with the modulation of several molecular markers of the immune and endothelial system. This modulation in addition to ameliorating the venous system functionality, which is objectively observed in most of the treated subjects (95-98%) and results in a reduction of the limbs heaviness sensation and of orthostatic oedema and cellulitis, exert a systemic effects, often also accompanied by an improved skin trophism.

Indeed, the "functional systemic therapy" (alternatively called also Functional Injective Treatment) with diluted polidocanol according to the present invention (so defined because it acts on the functionality of several organs and systems) does not result in a permanent parietal damage (vessel fibrosis), nor in cell death, as is in traditional sclerosant therapy. On the contrary, it activates the reticuloendothelial system, with the production of growth factors, as well as the immune system with the modulation of the levels of a number of cytokines and chemokines, associated with a higher overall well-being, which becomes apparent, for example, from a decrease in the seasonal infections, in the pain associated with chronic inflammatory events (such as rheumatoid arthritis) and in the improvement of articular mobility. According to a particularly preferred aspect, the invention is useful in the reduction of psoriasis skin rashes.

The effects on immunomodulation and inflammation markers make it understandable how, as opposed to what happens with the traditional sclerotherapy which results in a definitive and permanent parietal damage, using the present diluted polidocanol solution in non-sclerosing concentration, herein called Functional Injective Treatment (FIT) would result in long term positive effects.

Moreover, while traditional sclerotherapy, usually carried out with concentration up to 0.25% polidocanol, can result in side effects, such as pulmonary embolism, dyspnoea, dizziness, palpitations, vision disorders, headache, migraine, local paraesthesia, vasculitis, with incidence of from very rare (<0.001%) to rare (0.01-0.1%), deep vein thrombosis or limb pain, the concentrations of the treatment according to the present invention have very limited to zero side effects. There is almost no evidence even of quite common reactions (0.1-1%), such as superficial thrombophlebitis, allergic dermatitis, hives, erythema, skin necrosis.

Thus, without being bound to any particular theory, it is possible to hypothesize that, in such concentrations, polidocanol exerts a stimulation, instead of a sclerosis, of the venous endothelium, rightfully considered one of the richest live laboratory, with several aspects still unexplored by medical science, in which polidocanol in non-sclerosing concentration activates several responses that bring about an improvement of the inflammatory symptoms and inflammation clinical picture, with effects evident on the skin trophism directly linked with an improved microcirculation functionality.

Indeed, it has been found and measured, for example by means of photoplethysmography, that treatment with polidocanol can determine a decrease of the regional venous compliance, particularly in the lower limbs, with a significant decrease of the peripheral stasis (see example 5).

Furthermore, it has also been found that intravenous diluted polidocanol according to the invention is able to reduce a known marker of inflammation, the C-Reactive Protein (CRP) as well as some interleukins. The reduction in CRP levels is more consistent in subjects with autoimmune diseases, such as psoriasis, rheumatoid arthritis or systemic scleroderma and in the aged population, that usually has CRP levels above normal, due to osteoarticular conditions possibly associated with pain. Of note, this effect can be appreciated after a single treatment with the diluted polidocanol solution according to the present invention by Functional Injective Treatment (FIT).

b-FGF, PDGFbb, and VEGF are among the increasing growth factors, which could then be correlated with an improved venous system functionality, thus with the most visible cosmetic aspects. Increase of VEGF is particularly significant within the 1st and 7th day of treatment (p<0.01).

Among cytokines, IL-1β, IL1ra, IL-12 (p70) increase significantly (p<0.01), in particular within the 1st and 7th day of treatment. IL-7 decreases significantly up to 30 days and IL-8 increases in this same period of time (7-30 days).

Among chemokines, MIP-1α and MIP-1β showed a modest variation (increase) with respect to basal levels, particularly significant within the $1^{st}$ and $7^{th}$ days with respect to basal levels.

The most significant results are depicted in FIG. 1.

It is known that chemokines hold several functions in the immune system and can be secreted by endothelial cells themselves. It has also been demonstrated that some chemokines are able to ease the extravasation of circulating leukocyte, binding the heparan sulfate present inside the glycocalyx of endothelial cells. Thus, it has been now acknowledged that chemokines modulate and regulate inflammation in several body regions, also in the endothelium.

Figure 2A:
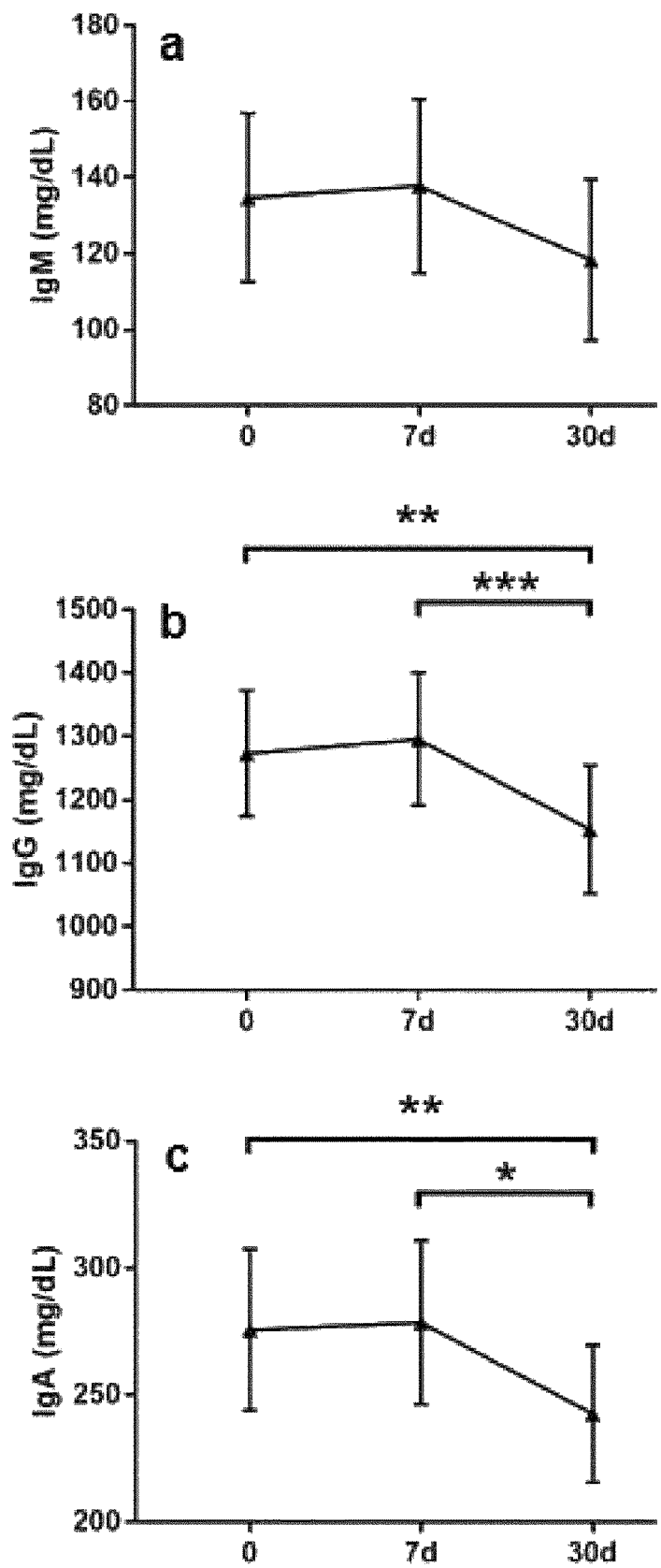
FIG. 2. Measurement of immunoglobulins levels at time zero (T0), one day (T1), 7 days (T7) and 30 days (T30) after treatment with diluted polidocanol according to the invention. Panel a): IgG, IgA, IgM; Panel b) light chains kappa/lambda, kappa, lambda.
Figure 2B:
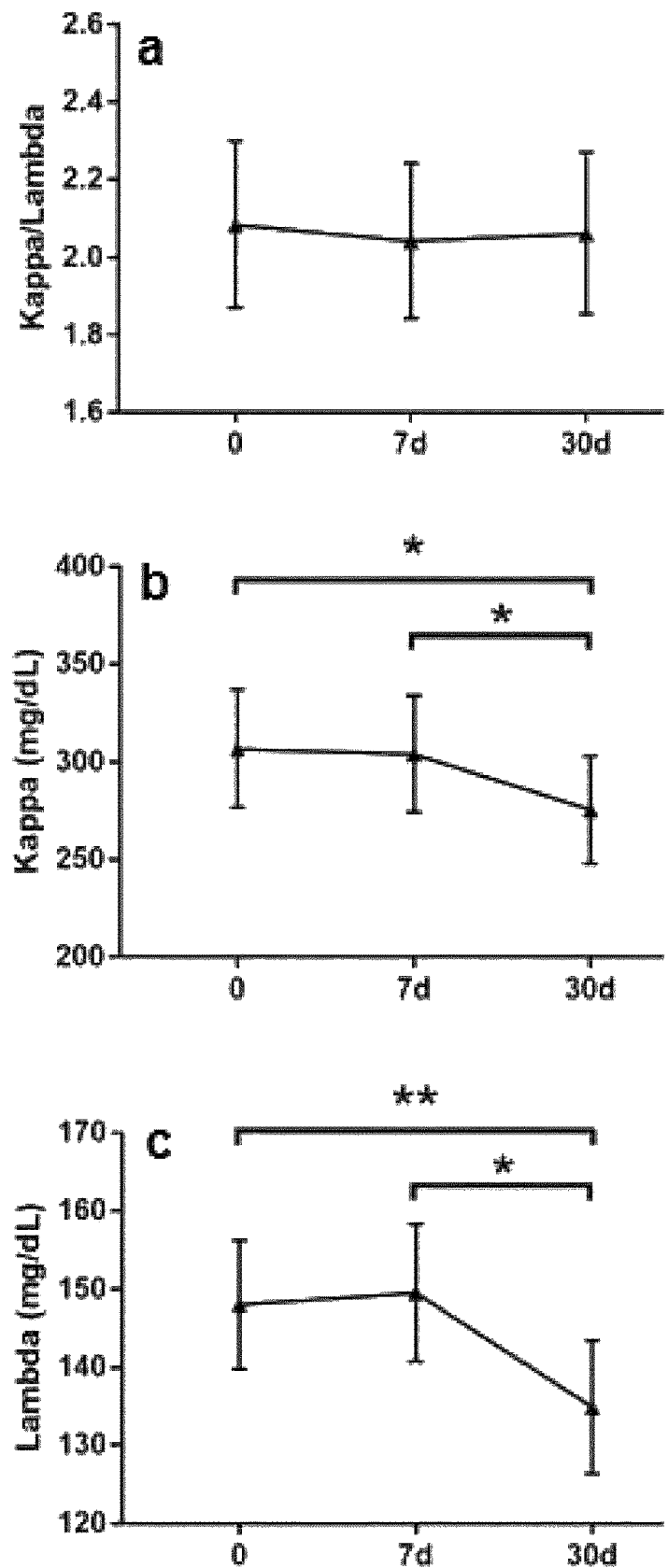

The decrease in the amount of serum immunoglobulins is another measurable effect; in particular it is significant between 7 and 30 days, when IgM, IgG, IgA and kappa and Lambda chains of the IgG light chains decrease. The results are shown in FIG. 2.

Thus, the present study offers proof that the treatment with diluted polidocanol not only does not result in an acute inflammatory response in the hours immediately following the treatment, but it is also associated with long term significant variations of a number of inflammatory (IL-1 ra and IL-1β, IL-7 and IL-8) and immunological (e.g. immunoglobulins levels) parameters, all of which have never been disclosed in relation to the traditional sclerosing treatment.

it is clear that, even though it is not possible to demonstrate a direct effect of the variation of each cytokine or each group of cytokines or growth factors on one or more aspects among those objectively found in most of the patients, it is indeed possible to speculate that the treatment with polidocanol in concentrations well below the minimum concentration presently commercially available, may activate the reticuloendothelial system modulating the immune system and resulting in a series of positive effects, among which a general anti-inflammatory activity.

The effects evidenced on healthy volunteers and on patients with chronic venous insufficiency from minor to severe, classified as C0 and C0s up to C3-C4 according to "Revision of the CEAP classification for chronic venous disorders: consensus statement." Eklöf B et al. J Vasc Surg., 2004, have been evaluated via QoL surveys (Quality of Life) approved and validated by the scientific community (Launois R. et al "Construction and validation of a quality of life questionnaire in chronic lower limb venous insufficiency (CIVIQ), Qual. Life Res., 1996, 5(6):539-554, and "Evaluation by Likert-type scale 4-point (0-absent, 1-moderate, 2-severe and 3-very severe) Elleuch et al. Adv Ther. 2016 September; 33(9):1536-49), filled in by the patient before the beginning of the treatment and at regular intervals (e.g. after 2, 4 or 6 therapy sessions).

The entity of the evidenced effects obviously depends on the total number of treatments carried out and on the body regions observed. For example, an improvement in the lower limbs skin appearance, i.e. of the regions directly treated, is already evident after 2 treatments, whilst after several treatments (12-14) in most cases (60%) an improved skin elasticity and a smoother skin, which is an indication of a better skin trophism, are observed both in general and, in 16% of cases, also in the face. For example, also the hair becomes shinier and easier to brush.

Therefore, a further aspect of the present invention is a composition comprising polidocanol in concentration below 0.1%, preferably of from 0.03 to 0.09% by weight, preferably of from 0.04 to 0.08%, preferably of 0.05%-0.06% in saline solution (0.9% w/V NaCl) for use as immunomodulating and anti-inflammatory agent. Said concentrations exert a non-sclerosing effect and are such that do not cause a venous, reticular or capillary parietal damage. Notably, on the other hand, polidocanol concentrations higher than or equal to 0.12% can still exert a sclerosing effect on small calibre capillary vessels or reticular veins.

More preferably, the polidocanol solution comprises a buffer, preferably bicarbonate buffer, in an amount not higher than 0.07% w/V. Even more preferably the bicarbonate buffer is sodium bicarbonate and it is in a concentration of from 0.05 to 0.06% w/V.

The buffered solution obtained is sterile and it is administered intravenously via injection in the reticular veins or capillary of the lower limbs. However, in order to obtain a reduction of the vein calibre, also brachial or hand veins can be treated.

In both lower and upper limb regions multiple injections are needed and are usually carried out in a volume never higher than 5 mL/injection for lower limbs reticular veins and 1 mL for the capillary region.

The product can also be prepared as a foam formulation via addition of a gas to the diluted polidocanol solution. The maximum dosage obtained is 24 mL and the minimum one is 12 mL. No clinical differences have been evidenced with either administration, even though the 10-12 mL administration is preferable in order to avoid or strongly limit the onset of even minor local complications. Thus, the maximum preferred volume is about 12 mL.

Thus according to a further aspect, the invention relates to a therapeutic and/or cosmetic treatment wherein compositions comprising polidocanol in concentration below 0.1% by weight, preferably of from 0.03 to 0.09%, preferably of from 0.04 to 0.08%, preferably of 0.05%-0.06% in saline solution (0.9% w/V NaCl), are used to stimulate a decrease in the venous stasis, both in the treated limbs and in the body and face, and as immunomodulating and anti-inflammatory agent. In particular, the compositions of the invention are useful in opposing the osteoarticular pain associated with a chronic inflammatory state and the related inflammation, particularly in the joints, such as in rheumatoid arthritis and in the psoriatic skin rashes.

EXPERIMENTAL PART

Example 1. Functional Injective Treatment (FIT) with Diluted Polidocanol

A commercially available polidocanol solution (Atossisclerol®) was diluted to 0.05% with a physiological saline solution. A 1.4% sodium bicarbonate solution was then added in order to obtain a final concentration of 0.06%. The patients, 80% of which were female between 18 and 82 years of age suffering from venous insufficiency from minor to severe, were subjected to treatment after obtaining their free and informed consent.

Before the treatment, about 100 patients were subjected to a survey in order to assess their quality of life and to evaluate possible variations of the phlogistic/inflammatory overall state, of the venous microcirculation and circulation functionality, and also, more in general, of the skin trophism.

After evaluating the survey answers, better described in examples 2 and 3, it was decided to thoroughly investigate the patients inflammation serum parameters and, more in general, the immunological state indicators, via measurement of cytokines, chemokines, immunoglobulins and several growth factors, on a limited number of patients, as better disclosed in examples 4 and 5.

Example 2. Evaluation of the Long Term Systemic Effects of Diluted Polidocanol: QoL Survey The long term systemic effects were evaluated via a survey given to patients after 3 or 4 treatments with diluted polidocanol.

In particular, they were asked to fill out a survey (CIVIQ-20) according to the criteria defined in Launois R. et al "Construction and validation of a quality of life questionnaire in chronic lower limb venous insufficiency (CIVIQ), Qual. Life Res., 1996, 5(6):539-554.

The survey contained the questions summarized hereinbelow, with answers indexed with values from 0 to 4 (0 if the feeling of discomfort described by the question was not applicable and from 1 to 4 if it was applicable with increasing intensity). Hereinbelow are collected the activities which turned out to be improved after the treatment:

1) During the last 4 weeks have you felt pain in the hips or legs and with what intensity? In 14% of cases a decrease in hip pain was observed after treatment with polidocanol according to the invention.
2) During the last 4 weeks have you had troubles in the routine work activities, due to troubles with the lower limbs? In 75% cases the patients could note a better condition during routine work activity
3) During the last 4 weeks have you had troubles sleeping due to troubles with your legs? With what frequency? 37% better sleeping conditions. No troubles.
4) During the last 4 weeks have you had troubles in the following activities due to troubles with your legs?
   a. Remaining standing for a long time. Improves in 87%
   b. Climbing several flights of stairs.
   c. Crouching kneeling down. Improves
   d. Walking at a brisk pace.
   e. Traveling by car, bus, plane. Improves in 85%
   f. Performing housekeeping tasks (ironing, walking around in the kitchen, etc.). Improves in 85%
   g. Going out at night. Improves in 85%
   h. Playing sports
5) Given that troubles with the legs can also affect moods, it was asked if during the last 4 weeks they had noticed troubles such as:
   a. Nervousness
   b. Quick fatigue
   c. Feeling of oppression
   d. Excessive caution
   e. Embarrassment in showing off the legs. Improves in 90%
   f. Irritability
   g. Feeling of being handicapped
   h. Morning fatigue. Improves in 95%
   i. Not feeling like going out. Improves in 75%.

The answers from the sample after the treatment, compared to those before the treatment, indicated that, overall in 87% of cases, the quality of life of the treated subjects improved.

Example 3. Likert Survey on the "Inflammatory" State in Treated Subjects

To the questions on the quality of life, 10 more specific questions were added in order to assess possible variations of the "inflammatory" state (n=100 patients) after the treatment. The survey was based on the indications of: "Evaluation by Likert-type scale 4-point (0-absent, 1-moderate, 2-severe and 3-very severe)" Elleuch et al. Adv Ther. 2016 September; 33(9):1536-49. Subjects were asked a self-assessment after each treatment and the results of the survey were evaluated after 8-10 months (i.e. after at least 4-5 treatments).

The survey was tailored on the Likert scale and aimed at evaluating the reduction of a number of symptoms related to chronic phlogosis, such as arthrosic or arthritis manifestations (both generic and autoimmune) with particular reference to articular mobility and pain, in subjects not suffering from full-blown diseases and apparently normal.

The answers were indexed according to a scale from 0 to 3 (or from 0 to 2).

1. Articular mobility

|  | Results % |
|---|---|
| 0: no variations | 13 |
| 1: 20% mobility improvement | 7 |
| 2: 50% mobility improvement | 78 |
| 3: 70% mobility improvement | 2 |

2. Reduction of pain related to chronic inflammatory events, in particular: cervical or lumbosacral arthrosis, and known rheumatic events to big and small joints (hips, knees, elbows, wrists, ankles and fingers). The results were as follows:

|  | Results % |
|---|---|
| 0: no variations | 20 |
| 1: 20% reduction of pain-related symptoms | 12 |
| 2: 50% reduction of pain-related symptoms | 68 |
| 3: 70% reduction of pain-related symptoms | 0 |

3. Reduction of symptoms and signs related to chronic degenerative pathologies of immune and inflammatory genesis (e.g. psoriasis, rheumatoid arthritis; n=12). The results were as follows:

|  | Results N. |
|---|---|
| 0: no variations | 2 |
| 1: 20% attenuation of manifestations related to skin and articular mobility | 5 |
| 2: 50% attenuation of manifestations related to skin and articular mobility | 4 |
| 3: 70% attenuation of manifestations related to skin and articular mobility | 1 |

4. Improvement of skin trophism (lower limbs and then of the whole body, face included). The results indicated that most of the patients recognized at least a slight improvement in skin appearance and elasticity, in 16% of cases also associated with an improvement of skin trophism of the face: as follows:

|  | Results % |
|---|---|
| 0: no variations | 5 |
| 1: slight improvement of the skin elasticity and of the trophism at the touch (smoother skin) in the lower limbs | 87 |
| 2: slight improvement of the skin elasticity and of the trophism at the touch (smoother skin) in the whole body | 60 |
| 3: improvement extended to the skin of the face | 16 |

5. Improvement of the hair trophism. The results were positive for 90%.
6. Reduction of infective events (influenza, tonsillitis, tracheobronchitis or upper respiratory tract infections, as compared to the previous year). The results were as follows:

|  | Results % |
|---|---|
| 0: no variations | 18 |
| 1: maybe less infective events | 12 |
| 2: definitely significant reduction | 70 |

7. Feeling of well-being for up to a 2 months period after the treatment. The results were as follows:

|  | Results % |
|---|---|
| 0: no variations | 12 |
| 1: I feel a bit better but I don't know | 32 |
| 2: I feel a bit better in the sense that I have a feeling of well-being | 30 |
| 3: life without the treatment is not the same, I feel the need to undergo treatment | 26 |

8. Feeling of lightness in the lower limbs. The results were as follows:

|  | Results % |
|---|---|
| 0: no variations | 2 |
| 1: lighter limbs | 70 |
| 2: lighter limbs and no oedema in the evenings | 28 |

The results were confirmed by photoplethysmography in a limited number of patients (n=20) wherein the measurement of venous refilling registered and examined, compared to the beginning of the treatment (after at least 4 sessions), has evidenced an increase of the peripheral venous refilling time in 17 out of 20 cases, indicating a plausible increase of venous resistance, i.e. a reduction of the peripheral reticulo-capillary bed or anyway of the superficial venous system.

9. Improvement of the so-called "cellulitis". The results were as follows:

|  | Results % |
|---|---|
| 0: no variations | 10 |
| 1: lighter limbs | 54 |
| 2: lighter limbs and no oedema in the evenings | 36 |

10. Improvement of the sleep-wake rhythm. The results were as follows:

|  | Results % |
|---|---|
| 0: no variations | 63 |
| 1: I don't know: maybe | 30 |
| 2: I'm sleeping better and wake-up more rested | 7 |

The results of the survey and of the objective exams indicate that there was an overall improvement of the patient's condition not only with regards to the venous system tonicity, but also, and surprisingly, with regards to an improved resistance to seasonal diseases and infections and to a decrease in the inflammatory symptoms of osteoarticular system pathologies. In these pathologies chronic pain resulted in an objective reduction in the quality of life according to what is disclosed for example in Launois R. et al "Construction and validation of a quality of life questionnaire in chronic lower limb venous insufficiency (CIVIQ)", Qual. Life Res., 1996, 5(6):539-554, which can be indexed, as well as its improvement, in a way that is considered to be sufficiently objective by the scientific community.

These results were confirmed and found to improve in long-term patients (i.e. patients followed for about three years who received about 15 treatments with polydocanol according to the invention).

Table 1 summarizes the percent individuals reporting an improvement of 50% after 4 or 15 treatments according to the invention, by self-assessment according to the Liked scale described above, for each of the following sign or symptom:

TABLE 1 self-assessment by the Likert scale

|  | % Results* (4 treatments) | % Results** (15 treatments) |
|---|---|---|
| 1. Articular mobility | 78 | 90 |
| 2. Reduction of pain | 68 | 82 |
| 3. Reduction of symptoms | 30 | 60 |
| 4. Skin trophism | 87 | 98 |
| 5. Hair | 90 | 95 |
| 6. Reduction of infections | 70 | 85 |
| 7. Feeing of wellness | 30 | 70 |
| Don't feel stopping treatment | 26 | 56 |
| 8. Feeling of lightness (lower limbs) | 70 | 98 |
| 9. Improvement of "cellulitis" | 54 | 86 |
| 10. Improvement of sleep-wake rythm | 30 | 56 |

*100 individuals
**200 individuals

Example 4. Serum Measurement of Cytokines and Other Inflammation Markers (CRP)

For serum measurements 12 healthy volunteer subjects were recruited, only having cosmetic telangiectasia problems to the lower limbs (C0, C1 and C2 stage), who did not take medications and from whom blood was drawn at time 0 and who were subjected to a treatment with diluted polidocanol, as described in example 1. The recruited patients had already been subjected to one or more polidocanol treatments, but had undergone a wash-out period of at least 4 months.

Blood was then drawn at about 30'-1 hour (T1h), 1 day (T1), 7 days (T7) and 30 days (T30) after treatment, measuring the following serum parameters:
 a) "Pro-inflammatory" cytokines: IL-1β, IL-6, IL-7, IL-12 (p70), IL-17, IFN-γ, TNF-α;
 b) "Anti-inflammatory" cytokines: IL-1ra, IL-4, IL-5, IL-9, IL-13;
 c) Chemokines: IL-8/CXCL8, IP-10/CXCL10, MIP-1α/CCL3, MIP-1β, RANTES/CCL5, Eotaxin/CCL11;
 d) Growth factors: b-FGF, PDGF-bb, VEGF, G-CSF.

Levels of IgM, IgG, IgA and of light chains kappa/lambda, kappa and lambda were also measured.

In a limited number of patients measurements 30 minutes and 3 hours after the treatment were carried out in order to identify short-term responses and assess possible acute inflammation indicators.

Determinations a)-d) were carried out with Multiple Immunomagnetic Assay (Bio-Plex, Bio-Rad). Ig determinations were carried out with commercially available kits.

22 out of 27 parameters were determined; however IL-2, IL-10, IL-15, GM-CSF and MCP-1/CCL2 were below the detection limits.

The determinations carried out were statistically analysed with the Friedman test and Dunns Multiple Comparison test. The most significant results are depicted in FIG. 1.

Overall the determinations showed that during the first hour after treatment (T30-45 min) most of the parameters (except for IP-10/CXCL10) resulted to be increased when compared with T0. However, the observed levels were in a range not significantly different from the controls made at 3 h or 24 h after the treatment (except for IL-12, IL-17, IL-4, IL-9, PDGFbb, bFGF, RANTES/CCL5).

None of the analysed parameters showed statistically significant differences in the comparison between the not-treated (T0) and 1 day after treatment (T1), indicating that the treatment does not induce endothelial or tissue damage resulting in an acute inflammatory reaction detectable with the detectability threshold of the assays used.

At 7 days post treatment (T7), pro-inflammatory cytokines IL-1β, IL-12 (p70), anti-inflammatory cytokine IL-1ra, chemokines MIP-1β/CCL4 and VEGF showed significantly increased serum levels, ascribable to a non-acute response. VEGF increases in a statistically significant way already from the 7th day post treatment and stays at higher levels with respect to those pre-treatment up to the 30th day.

At 30 days (T30) variations in the levels of IL-7 (decrease $p<0.01$), IL-1β, IL-1ra, IL-12, VEGF (increase: $p<0.05$) were statistically significant.

Thus, it is possible to conclude that the treatment with diluted polidocanol, in the conditions used, activates a systemic response wherein short-term (T7), and in some cases also medium term (T30), responses of a number of cytokines, chemokines and growth factors can be observed, which indicates a certain degree of immune system modulation.

Most of the analysed parameters showed a similar trend, characterized by increasing levels from T0, to T1 and T7 or similar levels from T0 and T1 and increasing at T7 (except for IL-13, IL-8/CXCL8, MIP-1α/CCL3).

The analysis of the Ig profile evidenced that none of the tested Ig fluctuates between T0 and T7, whilst at T30 IgA, IgM, IgG and lambda and gamma chains levels decrease with respect to T7 and T0 (see FIG. 2).

These results seem to highlight on one hand the absence of an immunogenic effect of polidocanol at the tested concentrations, evidenced by the lack of increase of IgM and IgG levels both after 7 and 30 days. Moreover, the aspecific decrease in all 3 Ig analyzed (IgA, IgG, IgM) suggests the hypothesis of a peripheral tolerance.

From the comparison between T7 and T30 it can be seen that there is an overall slight tendency of all the measured cytokines levels to increase. In particular, IL-12 (p70) increases significantly between T0 and T30, whilst cytokine IL-7 decreases in a statistically significant way between T0 and T30.

A similar approach was used in a limited group of patients with autoimmune diseases. 10 patients (5 with psoriasis, 3 with rheumatoid arthritis, 2 with systemic scleroderma) were administered once the composition of the invention and a sample of blood was taken at T1 (8 days), T2 (30 days) and T3 (60 days). Cytokine and CRP (C-Reactive Protein, an index of inflammation) levels were measured by SCREEN CRP TEST and compared to those at time 0 (before the treatment).

The results (average values) are shown in Table 2.

TABLE 2

Immunomodulatory activity of diluted polidocanol in autoimmune conditions

| Interleukins | T0 | T1 | T2 | T3 |
|---|---|---|---|---|
| 1 beta | 1 | 1.5 | 1.7 | 1.2 |
| 6 | 4.6 | 4.8 | 3.7 | 3.2 |
| 7 | 7 | 9 | 3 | 3 |
| 12 | 40 | 42 | 36 | 32 |
| 9 | 50 | 80 | 100 | 120 |
| 13 | 4 | 5 | 5 | 4 |
| 17 (25) | 40 | 45 | 32 | 28 |
| TNF alpha | 60 | 52 | 42 | 48 |
| CRP | 32 | 30 | 24 | 16 |

Figure 3:
FIG. 3. Treatment of peripheral venous insufficiency in a subject with psoriasis. The subject was treated with a single dose of diluted polidocanol 0.1%. Pictures were taken at T=0 (panel A) and after 30 days (panel B).

Of note, a single treatment with FIT was able to improve visibly the skin rashes in a subject with psoriasis (FIG. 3).

CRP levels in serum samples of individuals over 70 years old, chronically affected by osteoarticular problems, with or without pain, was also measured. CRP levels were measured within a group of 30 people, with a peripheral venous insufficiency. The subjects (23 females, 7 males) underwent sclerotherapy according to the invention. Then, CRP levels were measured at time 0 (beginning of treatment) at T1 (24 hours after treatment) and at T2 (8 days after treatment). Levels at T1 did not show any variation. On the contrary, at T2, 27 out of 30 individuals (90%), with exception of three individuals with low starting CRP levels (values comprised from 1-3 mg/l), showed a notable reduction In particular, in three cases where the starting CRP levels were 15, 18 and 27 mg/l the CRP levels were respectively reduced to 10, 9 and 16 mg/l.

This suggests that in the population over 70, with a constitutive higher inflammation index, the CRP index of inflammation is consistently reduced after a single treatment with a diluted polidocanol dose, intravenously.

Example 5. Venous Refilling Time Measurement Via Photoplethysmography Exam (FPG)

40 patients with C2 CEAP Class and bearing lower limbs varices were examined via photoplethysmography exam with a Photoplethysmograph with Light Reflection Rheography/1-Channel (Vasoquant 1000 D-Ppg), they were divided into two homogeneous groups wherein the venous refilling time was measured before and after the hemodynamic therapy.

In the Diluted Polidocanol Group the hemodynamic therapy was followed after 30 days by sclerosing treatment with diluted polidocanol, prepared as described in example 1. In the Basal Group, after hemodynamic therapy no further treatment was carried out.

In the Basal Group of 20 patients, measurements of the refilling time of the superficial veins (SV) via photoplethysmography (FPG) exam were carried out at time zero, at time 1 (1 month) after hemodynamic (surgical) therapy on the varices, and at time 6 (6 months) without any further treatment.

In the Diluted Polidocanol Group of 20 patients, measurements of the refilling time of the SV via FPG were carried out at time zero, at 1 month after hemodynamic (surgical) therapy on the varices, and at time 6 (6 months) after 3-4 sessions of sclerotherapy with the method of the invention.

Figure 4:
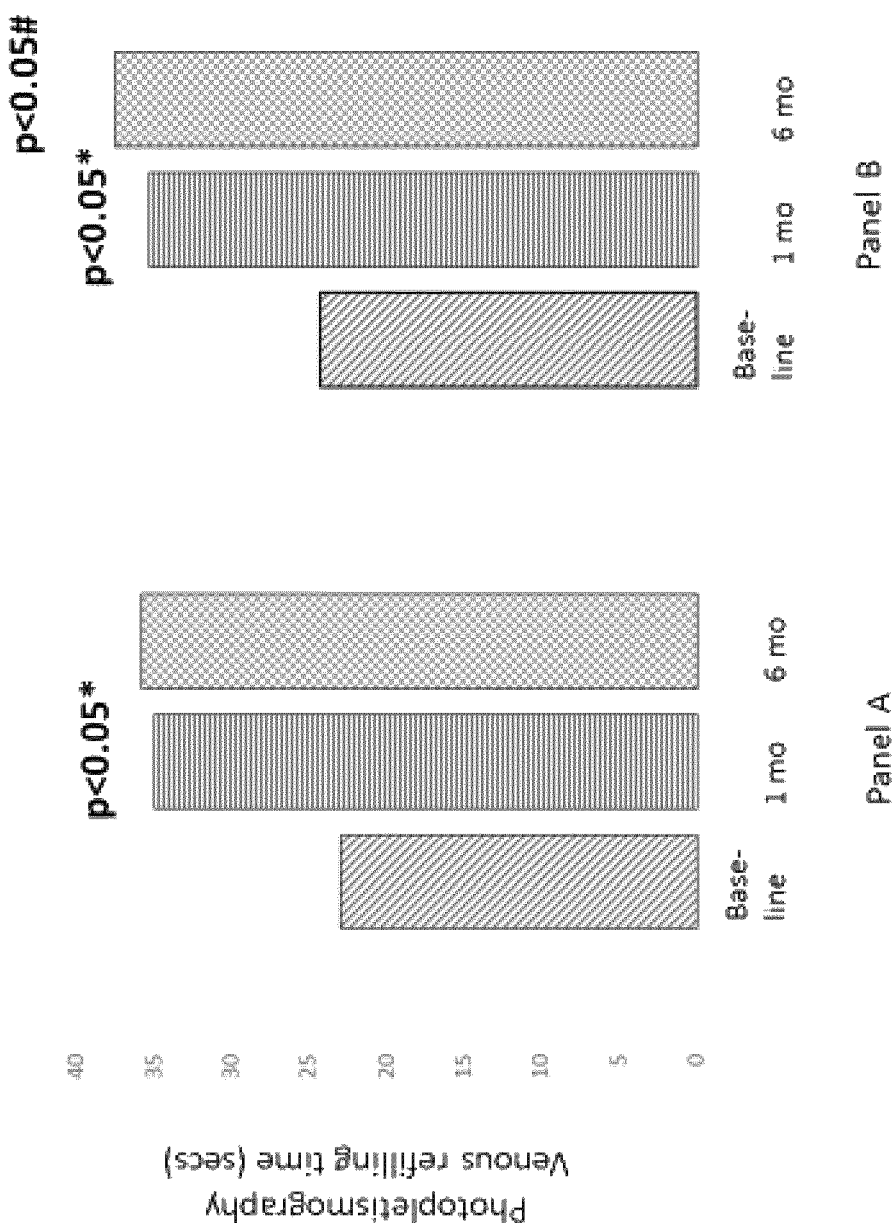
FIG. 4. Measurement of venous refilling time by photoplethysmography. Panel A: control, Panel B: treatment according to the invention at T0 (baseline) and after 1 month and 6 months. *p<0.05 vs. baseline; #p<0.05 vs. 1 mo (t-student).

Results are depicted in FIG. 4: the difference between the basal group at T6 and the Diluted Polidocanol Group at T6 was statistically significant for an increase in the refilling time from 35 to 38 seconds (p<0.001 Chi-squared test). In particular, statistical analysis proved that in subjects treated also with polidocanol the venous refilling time (VRT) significantly improved both at 1 month and at 6 months after the treatment (1 month vs basal: 35.3±4.14 vs 24.3±6.78, p<0.05; 6 months vs 1 month: 37.6±4.13 vs 35.3±4.14, p<0.05). In the control the improvement was less evident and the difference of VRT at 1 month was not significantly different from the values at 6 months.

The number of patients with an improved index according to FPG exam at 6 months after 3-4 sessions with diluted polidocanol (pol/dil) with respect to the Basal Group was as follows:

Diluted Polidocanol group: 18 out of 20 (90%)
Basal Group: 4 out of 20 (25%)

Therefore, it is possible to conclude that the treatment with diluted polidocanol according to the invention results in a progressive decrease of the calibre of the superficial veins system, with a progressive reduction of the venous stasis, significantly more evident than in subjects treated only with surgical/hemodynamic treatment.

The invention claimed is:

1. A method for reducing osteoarticular pain or inflammation, comprising intravenously administering to a subject in need thereof polidocanol as the only active agent in a concentration (w/V) of from 0.03% to 0.09%.

2. A method according to claim 1, wherein said polidocanol is administered in a concentration of from 0.04 to 0.08% (w/V) in a saline solution.

3. A method according to claim 1, wherein said polidocanol is administered with a buffer agent.

4. A method according to claim 3 wherein said buffer is sodium bicarbonate.

5. A method according to claim 1, wherein said polidocanol is administered in a concentration of from 0.05% to 0.06% in a saline solution (0.9% w/V NaCl).

6. A method according to claim 3 wherein said buffer is sodium bicarbonate in final concentration below 0.07% w/V.

7. A method according to claim 3 wherein said buffer is sodium bicarbonate in final concentration of from 0.05% to 0.06% w/V.

8. A method according to claim 1, which is for reducing osteoarticular pain and wherein said subject is suffering from osteoarticular pain.

9. A method according to claim 1, which is for reducing inflammation and wherein said subject is suffering from inflammation.

* * * * *